United States Patent [19]
Hogan

[11] Patent Number: 5,490,411
[45] Date of Patent: Feb. 13, 1996

[54] TESTING DEVICE FOR SURFACES SUBJECT TO IMPACT

[76] Inventor: Paul Hogan, 36 Sycamore La., Phoenixville, Pa. 19460

[21] Appl. No.: 266,944

[22] Filed: Jun. 27, 1994

[51] Int. Cl.⁶ ................................... G01N 3/30
[52] U.S. Cl. ........................ 73/12.13; 73/12.01; 73/78
[58] Field of Search ................. 73/12.01, 12.04, 73/12.06, 12.09, 12.11, 12.13, 12.14, 78, 79, 81, 82, 84, 658, 517 R

[56] References Cited

U.S. PATENT DOCUMENTS

| | | | |
|---|---|---|---|
| 3,298,222 | 1/1967 | Costello et al. | 73/12.13 |
| 3,380,294 | 4/1968 | Redmond | 73/12.13 |
| 3,421,364 | 1/1969 | Moneypenny et al. | 73/82 |
| 4,384,487 | 5/1983 | Browning | 73/517 B |
| 4,640,120 | 2/1987 | Garritano et al. | 73/12.13 |
| 4,856,318 | 8/1989 | Hogan et al. | 73/12.13 |

FOREIGN PATENT DOCUMENTS 1569730  6/1990  U.S.S.R. .................... 73/1 D

Primary Examiner—R. Raevis
Attorney, Agent, or Firm—Eugene E. Renz, Jr.

[57] ABSTRACT

A testing device for surfaces subject to impact, comprising a transducer module and an electronics module cooperatively connected together. The transducer module includes an impact head for impact generally in the z-axis of a surface defined by an x and y-axis, and a transducer including an accelerometer aligned with the x, y and z axes for producing a voltage output proportional to the acceleration in each of the axes upon impact by the impact head on a surface. The electronics module includes a voltage source for supplying electrical energy and computer powered by the voltage source for vectorially adding the voltage output to determine the peak acceleration upon impact independent of the actual orientation of the impact head on the surface.

6 Claims, 2 Drawing Sheets

TESTING DEVICE FOR SURFACES SUBJECT TO IMPACT

FIELD OF THE INVENTION

This invention relates to a testing device for surfaces such as playground surfaces and the like which are potentially subject to impact by humans. More specifically, the invention relates to a surface resiliency tester device including a transducer module for measuring the acceleration produced upon impact by the module on the surface and an electronic module which calculates the acceleration based upon the measurements taken by the transducer module.

BACKGROUND OF THE INVENTION

Each year many thousands of children and adults are injured in playgrounds, and in public and private recreation and sports facilities, due to falls on inadequately prepared surfaces. Lawsuits in which damages reach several million dollars are common where playground accidents have occurred. Insurance companies are being much more selective in granting coverage and, in some instances, are denying liability protection to institutions.

According to the U.S. Consumer Product Safety Commission more than 150,000 persons are injured each year on playgrounds in the United States. The need for a systematic and consistent means for evaluating the surface materials and to provide accessibility by handicapped individuals to playgrounds has been further amplified by the passage of the Americans With Disabilities Act.

There is an increased awareness of the need for playground safety, not only because of the litigation and because of direct government intervention, but also because institutions are recognizing that something needs to be done.

In many instances, there are materials that currently exist that will adequately protect the children and adults from damage. Some proposed methods to test these materials are extremely expensive, however, and others are relatively cheap. No uniform guidelines exist as to amounts and thickness of these materials, to reduce the desired safe level of acceleration in the event of a fall. Accordingly, each installation must be evaluated both as it is installed and over a period of time as constant use by playground users may change the properties of the installed surface.

A method and apparatus for determining the suitability of playground, recreation and sports facility surfaces has been provided in HOGAN, et al U.S. Pat. No. 4,856,318. The apparatus includes a transducer module consisting of an impact head and a transducer capable of converting impact forces to electrical signals. The device also includes an electronic module which detects the electrical signal from the transducer, processes it and converts it to a numerical reading. In the HOGAN Patent, a transducer is fixed to an impact head mass along a vertical center line which is on or slightly above the center of gravity. The transducer produces an electrical output signal at the moment of impact that is proportional to the peak impact G-level. This signal is detected at its peak, and operated on to covert the signal to a G-level indication.

Devices of the type described in the HOGAN Patent have been successful at least for preliminary data sampling. However, the device is severely limited for several reasons. First, it is very directional and does not produce a true reading unless the drop is truly on the perpendicular axis. Also, there often are significant variations in surface levelness. As a result, there really is no way to be sure that the drop was within the linear limits of the device. Multiple drops will generally produce a consistent or average reading if the drops are all within ±5% of the vertical. However, if the surface is not truly horizontal, then even truly vertical drops are not able to produce acceptable data.

It has now been discovered that merely measuring the gravitational force generated by impact of a device on a surface without being able to process the information to produce meaningful interpretive results is not enough to fully evaluate the surface. For example, in addition to the maximum gravitational force seen during the impact, the duration of the impact is also of interest. Specifically, the gravitational force as a function of the impact time produces what is known as a severity index (SI), which is the force measured divided by the amount of time needed to generate the maximum impact force. The United States Consumer Product Safety Commission Playground Safety Handbook now recommends a surface resiliency for playgrounds of 200 g, a SI of 1,000 and a head injury criteria value (HIC) of 1,000. While the calculation of an HIC value for a given drop involves complicated mathematical calculations, it would be desirable to make the measurements necessary for such calculations and, hopefully, be able to store sufficient data for the series of calculations.

Accordingly, it is the object of this invention to provide a testing device for surfaces subject to impact which is capable of producing reproducible accurate values relating to the impact.

Another object of this invention is to provide such a device which can accommodate variation in the relationship of the surface to the horizontal.

Yet another object is to provide a device which is capable of measuring and storing the data necessary to calculate specific head injury criteria as defined by various government and safety agencies. Other objects will appear hereafter.

SUMMARY OF THE INVENTION

It has now been discovered that the above and other objects of the present invention may be accomplished in the following manner. Specifically, an improved testing device for surface subject to impact has been discovered. The device includes a transducer module and an electronics module cooperatively connected together. The transducer module includes an impact head for impact generally along the z-axis of a surface defined by an x and y axis. The transducer module includes an accelerometer means aligned with the x, y and z axes for producing a voltage output proportional to the acceleration in each of those axes upon impact by the impact head on the surface. The electronics module supplies its own electrical energy from a voltage source and includes a computer means powered by the voltage source to vectorially add the voltage output to determine acceleration of the transducer module upon impact independent of the actual orientation of the impact head on the surface.

In a preferred embodiment, the transducer module has an axially aligned handle and a shaped impact head for impact generally in the z-axis of a surface defined by an x and y axis. The impact head encloses an accelerometer which produces an analog signal proportional to the force experienced at impact in each separate axis. This signal is transmitted through the connecting electrically conductive cord to the electronic module which amplifies the analog signal and converts it to a digital signal. The electronic module also includes a computer along with key-pad means for providing input into the computer. Display means are provided as well so that the output and other information from the computer can be visually inspected during the tests. An alternative means for connection between the two modules is the use of radio means to transmit the data from the impact or transducer module to the computer.

The computer itself is preferably adapted to monitor the conditioned digital signals and collect data upon detection of an initial acceleration above a predetermined value. This then produces a data stream for the impact to permit calculation of head injury criteria from the data stream. In a preferred embodiment, the computer monitors the conditioned signal by taking a plurality of samples per second for each axis, such as for example 10,000 samples per second per axis, and thereafter saves data for a time beginning a predetermined period, such as 1 millisecond, before the signal exceeds a predetermined value to a predetermined time, again, such as 1 millisecond, after the signal returns below a predetermined value. This collection of data forms a drop data base. In one embodiment, it is desirable to have the computer scan the drop data collection in intervals of time to determine the time of the maximum acceleration per unit of time. Simultaneously, the computer is adapted to scan the drop data collection to determine peak acceleration. Both maximum acceleration per unit time and peak acceleration may be then used to determine the head injury criteria, SI and HIC, and other useful information. The resulting data can be displayed on the display screen, including the oscilloscope form of the graph. In this manner, the test can be visually evaluated on site.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figure 1:
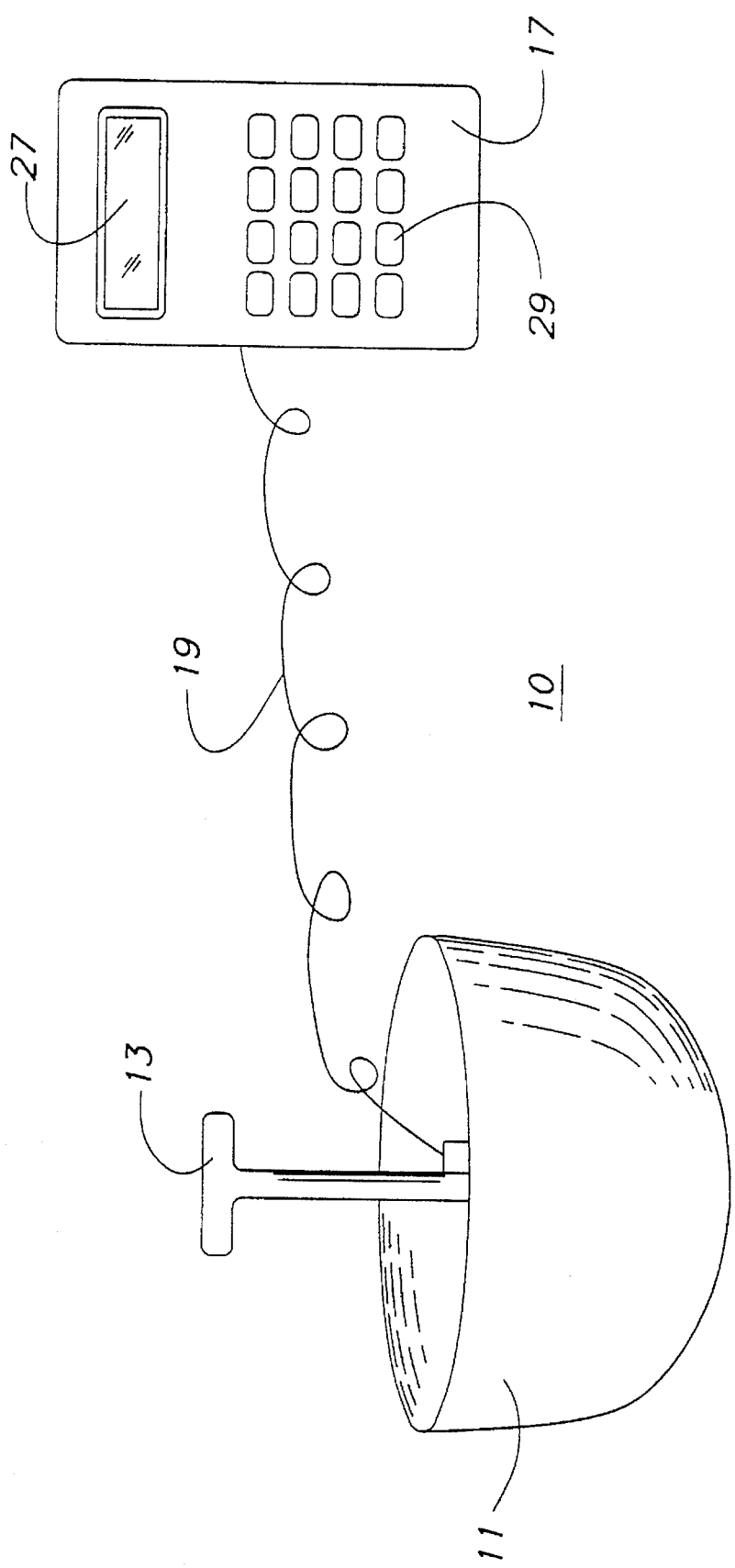
FIG. 1 is a perspective view of the device of this invention, illustrating the two modules of this invention and the connecting electrical cord.

The device of the present invention, shown generally by reference numeral 10 in FIG. 1 consists of a transducer module 11 which is adapted for drop testing. The resiliency or hardness of playground, recreational or other types of surfaces or soils where the condition of the surface or soil may be the most influential factor in the degree of trauma caused by an accidental fall. A handle 13 is provided for carrying the transducer module 11 and for aligning the module prior to its being released for impact with the surface. An electronics module 17 is operably connected to the transducer module 11 by an electrically conductive cord 19. Cord 19 is fastened to the transducer module 11 at a point close to the axis of handle 13 so as to provide at most a minimum amount of disturbance to the transducer module 11 as it falls to the surface being tested. Also for that reason, the cord is made of coiled cord which expands easily without measurable pull on the transducer module.

The transducer module 11 includes a three axis accelerometer transducer which is aligned with the x, y and z axis. The axes are defined by the direction of drop onto the surface of interest. Specifically, the transducer module drops under the force of gravity (y) in the z-axis of a surface defined by an x and y axis. The accelerometer 15 produces a voltage output proportional to acceleration in each of these three axes upon impact of the impact head of module 11 on the surface. This voltage output is transmitted via cord 19 to electronics module 17, shown schematically in FIG. 1 as an enclosed unit having a display 27 and key-pad 29. Module 17 is shown in greater detail in FIG. 2.

The acceleration transducer 15 employed in the preferred embodiment of the present invention is a piezoelectric three axis transducer manufactured by PCB. Transducer 15 provides a voltage output in the form of an analog signal which is proportional to the force experienced at impact. The signal is generated over a period of time and represents acceleration from an essentially at rest condition during free fall which is subjected to a force upon impact as the transducer module strikes the surface and comes to rest.

The analog signals are transmitted from transducer 15 via connecting cord 19 to provide an input into electronics module 17. As noted previously, radio signals may alternatively be used. A signal is first conditioned by a three channel class 1000 input signal conditioner 21 which transmits the signal to a three channel analog to digital converter. The converter 23 provides a conditioned signal to microcomputer 25. Power for the tri-axial acceleration transducer 15 is supplied through cord 19 by a power source described herein below. Of course, an on board battery would be needed if a radio is used.

Acceleration transducer 15 is a piezoelectric accelerometer that conveniently fits within the cavity constructed to receive it in the transducer module 11. The accelerometer generates an electrical signal which is proportional to the acceleration or deceleration that is experienced by the transducer. The accelerometer outputs a specific calibrated number of millivolts per gravity output. A constant current source diode supplies a four milliamps current to establish the quiescent operating point of the accelerometer. As the accelerometer experiences acceleration, the voltage output varies by an amount equivalent to 0.01 volts per unit of gravity. This voltage is the primary measurement signal and is processed as described herein below.

The particular micro computer employed in the preferred embodiment described herein is an Intel 80C188EB microprocessor using Microsoft C7 programming language to provide compatibility with readily available IBM compatible personal computers.

For each accelerometer signal coming from the transducer 15 and band pass filtered with a cut off frequency of 100 Hz in conditioner 21, a minimum sample rate is 2000 Hz. The microprocessor has a sampling rate of 10 Khz per channel, resulting in an aggregate sampling rate of 30 Khz when all three channels are being considered. This sampling rate is sufficient for calculations and yet within the bounds of data acquisition without timing based loss.

Channel notations are assigned to the z axis for the primary access, perpendicular to the impact surface, and x for the axis parallel to the minor axis of the ovoid design of the transducer module impact head 11. Y is, of course, the axis parallel to the major axis of the ovoid. X and y form a plane which is parallel to the impact surface so that on the occasions when the impact surface is directly in line with the z axis, all of the forces will be in that axis and the x and y axes will have a zero force component.

When a drop test is started, the system starts sampling the three input channels and storing the unscaled digital data in a circular memory buffer forming part of the microcomputer 25. The data from the z axis is continually monitored to determine if its output indicates 10 G deceleration. When the 10 G point is detected, the current position of the buffer is marked as the start of the drop data and the impact is considered to have started. The system continues to record the next 190 samples for each channel, after which the sampling is terminated. The start point of the buffer is actually the 30th sample in the buffer and serves as post-trigger view function. The resulting data set is 220 points per channel, with a 10 Khz sampling rate yielding a recording time of 22 milliseconds. Testing has shown that this is sufficient time for most impacts to decay to zero force.

The x and y data points are vectorially summed on a point-by-point basis to form an off axis force vector which in turn is summed with the z-axis data, itself a vector, to yield a total impact force vector. The peak gravitational force is then determined from the total force vector by a simple peak detect algorithm. The severity index is then calculated using discrete techniques. First, each point of the total force vector is raised to the 2.5 power and all 220 resultants are summed. The summation is then divided by the total sample times, 220 milliseconds, to yield the severity index. The angle of the drop is, of course, the inverse tangent of the off axis drop vector and the z-axis drop vector.

A microprocessor or computer 25 is provided with a LCD text and graphic display 27. Input to the computer 25 is done by an alpha-numeric key-pad 29. Within the computer is a real time clock 31 and a non-volatile data storage bank 33. A RS 232 communication port is provided for access to a host computer.

The present invention provides a significant advantage in the power supply section of the device of this invention. The function of the power supply is to convert the voltage of a battery to the various voltages required by the circuits. A rechargeable battery pack 37 is provided, typically being a five cell nickel cadmium head battery with an output voltage of 6 volts. The nickel cadmium batteries are rechargeable, using a battery charger circuit 39 which derives current from a wall cube 41. In order to insure accuracy, it is necessary for the voltages needed by the various parts of the circuit to remain constant, even as the battery is discharged during use. To accomplish this, a DC to DC converter 43 is employed. In the embodiment shown in FIG. 2, a Maxim MAX715 is used in addition to a MAX630 which generates the 20 voltage exitation needed by the accelerometers. Multiple output voltages are provided from the converter 43 via line 45 to all of the circuits. Specifically the microcomputer 25 requires a five volt source for itself and related logic. 15 volts and −5 volts are used in the conditioner 21. The accelerometers require 20 volts and the LCD display 27 requires a power source of −21 volts. Once the testing has been completed, data can be transferred via port 47 to a host computer.

Figure 2:
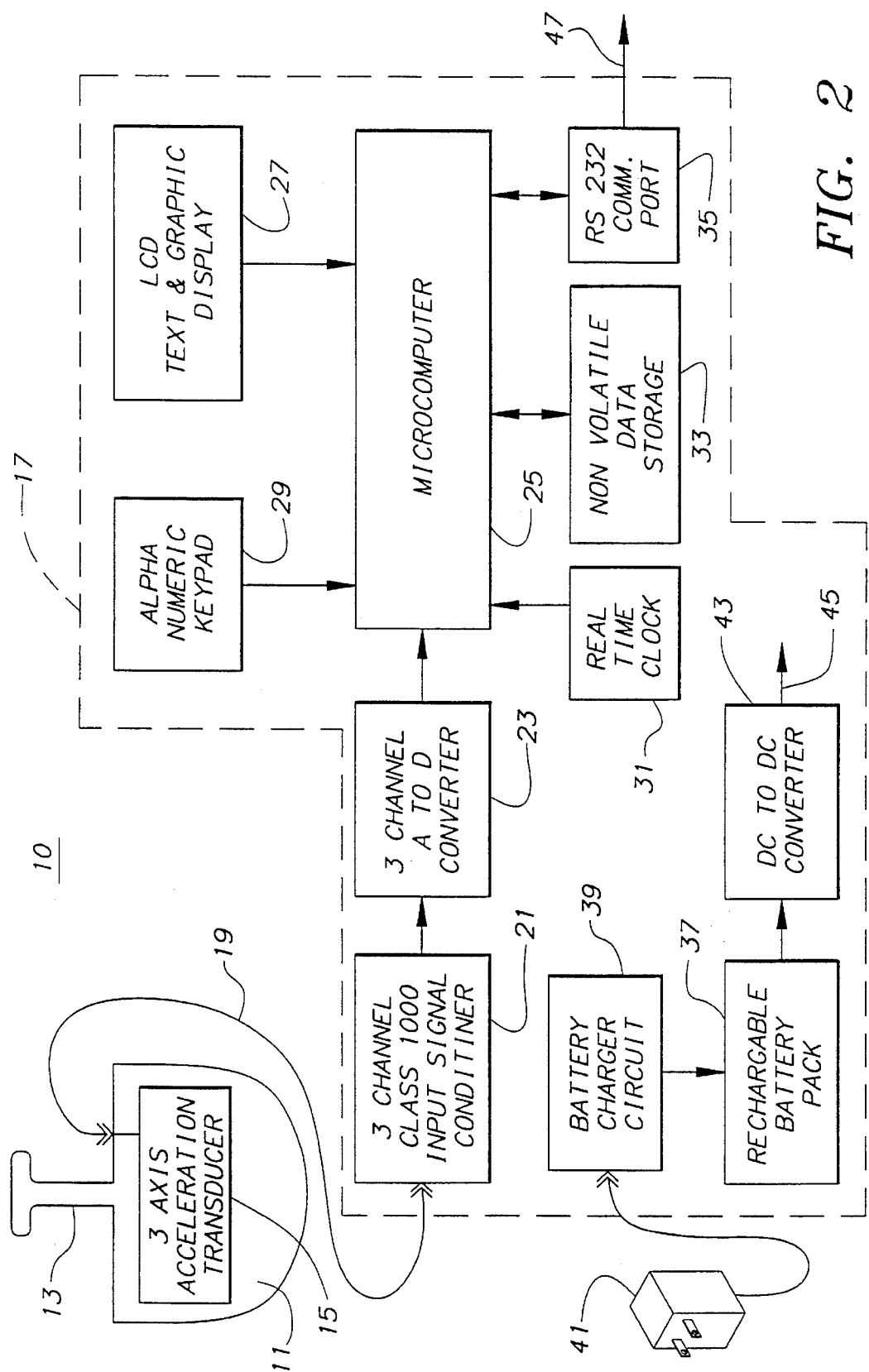
FIG. 2 is a block diagram of the device shown in FIG. 1, illustrating the operation of the two modules in cooperation.

In order to demonstrate the efficacy of the present invention, a number of tests were performed using the devices shown in FIGS. 1 and 2. The device was first calibrated by injecting a half sign of known amplitude and duration. For such a wave form the peak acceleration, the SI and the HIC values are easily computable.

The half sine wave was then applied to each analog input channel independently to display peak SI and HIC value which in turn was verified against the manually calculated results. The half sine wave was then applied to coupled channels to verify the vector processing algorithms. The display illustrated the output as a graph.

Final system verification was performed by comparing the impact data obtained with the present invention to date obtained by an existing laboratory model impact tester. Sample drops were conducted by an independent testing service using a laboratory model impact tester from heights 3 feet, 6 feet and 8 feet on two separate materials. The first was a two foot square two inch rubber mat typically of the type used for institutional playgrounds. The other material was a box of pea gravel, eight inches deep and having 2 square feet of area. A very satisfactory correlation between data from the device of the present invention and the laboratory test data was achieved.

What is claimed is:

1. A testing device for surfaces subject to impact, comprising:

a transducer module and an electronics module cooperatively connected together;

said transducer module having an axially aligned handle and a shaped impact head for impact generally in the z-axis of a surface defined by an x and y-axis, said shaped impact head comprising an accelerometer means aligned with each of said axes for producing a voltage output proportional to acceleration in each of said axes upon impact by said impact head on said surface, said accelerometer means having an accelerometer for producing an analog signal proportional to force generated by said impact;

said electronic module having a means for supplying electrical energy to said electronic module, an amplifier, and an analog to digital converter for converting analog signals to conditioned digital signals and computing means for vectorially adding said conditioned signals to determine a peak acceleration of said impact head independent of orientation of impact of said impact head on said surface, said computing means comprising key-pad means for providing input into said computing means and display means for displaying output from said computing means, said computing means adapted to monitor said conditional signals and to collect data upon detection of an acceleration of said impact head above a predetermined value by taking a plurality of acceleration samples of said impact head per second for each axis and saving data for a predetermined period before said conditioned signals exceed a predetermined value to produce a data stream from said impact for use in calculating head injury criteria from said data stream, said computing means being programmed to save data from about one millisecond before said conditioned signals exceed said predetermined value to about 1 millisecond after said conditioned signals return to below said predetermined value to form a drop data collection, and calculating said head injury criteria from said drop data collection.

2. The device of claim 1 wherein said computing means monitors said conditioned signal by taking about ten thousand samples per second for each axis and saving data for said predetermined period before said conditioned signal exceeds said predetermined value thereby to form a drop data collection.

3. The device of claim 2 wherein said computing means scans said drop data collection in intervals of time to determine the time of the maximum acceleration.

4. The device of claim 3 wherein said computing means scans said drop data collection to determine said peak maximum acceleration.

5. The device of claim 1, wherein said modules are connected using an electronically conductive cord.

6. A testing device for surfaces subject to impact by a human head comprising a transducer module having an axially aligned handle and an impact head for impact upon a surface defined by an x and y-axis generally in a z-axis of said surface, said transducer module having an accelerometer for producing analog signals proportional to force generated by said impact, and an electronics module cooperatively connected to said transducer module for convening said analog signals to conditioned digital signals and it computing means for vectorially adding said conditioned signals to determine a peak acceleration of said impact head upon impact independent of direction of said impact by said impact head on said surface, wherein:

said computing means is adapted for monitoring said conditioned signals and for collecting data upon detection of an acceleration of said impact head above a predetermined value by collecting a plurality of acceleration samples per second of said impact head for each axis for a predetermined period of time before said conditioned signals exceed said predetermined value to a predetermined period of time after said predetermined value to produce a dam stream from said impact for use in calculating head injury criteria from said data stream, said computing means being programmed to save data from about one millisecond before said conditioned signals exceed a predetermined value to about one millisecond after said conditioned signals return to below said predetermined value thereby to form a drop data collection, and head injury criteria from said drop data collection.

* * * * *